US010925285B2

(12) United States Patent
Kaneko et al.

(10) Patent No.: US 10,925,285 B2
(45) Date of Patent: Feb. 23, 2021

(54) PATHOGEN AND PEST EXTERMINATING DEVICE AND REACTION VESSEL THEREOF

(71) Applicant: TOHOKU UNIVERSITY, Sendai (JP)

(72) Inventors: Toshiro Kaneko, Sendai (JP); Keisuke Takashima, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 235 days.

(21) Appl. No.: 16/328,467

(22) PCT Filed: Aug. 29, 2017

(86) PCT No.: PCT/JP2017/030881
§ 371 (c)(1),
(2) Date: Feb. 26, 2019

(87) PCT Pub. No.: WO2018/043468
PCT Pub. Date: Mar. 8, 2018

(65) Prior Publication Data
US 2020/0178536 A1 Jun. 11, 2020

(30) Foreign Application Priority Data
Aug. 30, 2016 (JP) ............................ JP2016-167911

(51) Int. Cl.
*A01N 59/00* (2006.01)
*A61L 2/14* (2006.01)
(Continued)

(52) U.S. Cl.
CPC ................ *A01N 59/00* (2013.01); *A61L 2/14* (2013.01); *A01N 25/02* (2013.01); *A23L 3/26* (2013.01);
(Continued)

(58) Field of Classification Search
CPC ........... A01N 59/00; A01N 25/02; A61L 2/14; A61L 2/208; A61L 2202/122;
(Continued)

(56) References Cited

FOREIGN PATENT DOCUMENTS

CN 104883881 A 9/2015
EP 2 941 955 * 11/2015 .............. A01M 1/00
(Continued)

OTHER PUBLICATIONS

Jun. 3, 2020 Office Action issued in Chinese Patent Application No. 201780052437.1.
Oct. 10, 2017 International Search Report issued in International Patent Application No. PCT/JP2017/030881.

*Primary Examiner* — Jennifer Wecker
*Assistant Examiner* — Jonathan Bortoli
(74) *Attorney, Agent, or Firm* — Oliff PLC

(57) ABSTRACT

A pathogen and pest exterminating device that can efficiently exterminate pathogens and pests in a shorter time. One electrode includes a part to be inserted into a reaction vessel, and other electrode is arranged in a position that opposes the insertion part. A water supply unit is provided to supply water to the reaction vessel through the insertion part, and a gas supply unit provided of supplying gas, which will become plasma, to the reaction vessel. A power supply unit is provided to be capable of applying voltage between the insertion part and the other electrode such that OH radicals are generated inside the reaction vessel to which the water and the gas are supplied. The insertion part is formed in a shape that restricts, between itself and the other electrode, a flow rate of water from the water supply unit such as a coil, waveform, or mesh shape.

14 Claims, 6 Drawing Sheets

(51) Int. Cl.

| | |
|---|---|
| ***A01N 25/02*** | (2006.01) |
| ***A61L 2/20*** | (2006.01) |
| ***A01M 17/00*** | (2006.01) |
| ***H05H 1/24*** | (2006.01) |
| ***A01G 2/00*** | (2018.01) |
| *A23L 3/26* | (2006.01) |

(52) U.S. Cl.
CPC ......... *A61L 2/208* (2013.01); *A61L 2202/122* (2013.01)

(58) Field of Classification Search
CPC ....... A61L 2202/11; A23L 3/26; A01M 17/00; H05H 2245/1225; H05H 2001/2456; H05H 2001/245; H05H 2001/2468; H05H 2001/2443; H05H 1/2406; A01G 2/00
See application file for complete search history.

(56) References Cited

FOREIGN PATENT DOCUMENTS

| | | | |
|---|---|---|---|
| JP | 2000-107754 | A | 4/2000 |
| JP | 2001-145689 | A | 5/2001 |
| JP | 2004-359307 | A | 12/2004 |
| JP | 2009-054557 | A | 3/2009 |
| JP | 2015-192621 | A | 11/2015 |
| JP | 5909831 | B2 | 4/2016 |
| KR | 10-1402935 | B1 | 6/2014 |
| WO | 2007/105330 | A1 | 9/2007 |
| WO | 2009/060214 | A1 | 5/2009 |
| WO | 2014/104350 | A1 | 7/2014 |

* cited by examiner (a)

(b)

(a)

(b)

(a)

(b)

PATHOGEN AND PEST EXTERMINATING DEVICE AND REACTION VESSEL THEREOF

FIELD OF THE INVENTION

The present invention relates to a pathogen and pest exterminating device, and a reaction vessel thereof.

DESCRIPTION OF RELATED ART

Conventionally, a pathogen and pest exterminating device has been developed by the inventors of the present invention. This pathogen and pest exterminating device includes a reaction vessel, a pair of electrodes, a water supply unit, a gas supply unit, and a power supply unit. One of the electrodes includes an insertion part to be inserted into the reaction vessel, the other electrode is arranged in a position that opposes the insertion part, the water supply unit is provided so as to be capable of supplying water to the reaction vessel through the insertion part, the gas supply unit is provided so as to be capable of supplying gas, which will become plasma, to the reaction vessel, and the power supply unit is provided so as to be capable of applying voltage between the insertion part and the other electrode such that OH radicals are generated in the reaction vessel to which the water and the gas are supplied (for example, see Patent Literature 1).

CITATION LIST

Patent Literature 1: JP-B-5909831

SUMMARY OF THE INVENTION

Since the pathogen and pest exterminating device described in Patent Literature 1 introduces not only the gas but also the water into the reaction vessel, the OH radicals can be efficiently generated, and thus it is excellent in extermination effects of pathogens and pests. When this exterminating device is used in the field of agriculture and the like, it is desirable that the OH radicals are generated as much as possible per unit time, such that the extermination of pathogens and pests can be performed quickly and efficiently.

The present invention was made by focusing on such objective, and an objective thereof is to provide an exterminating device that can efficiently exterminate pathogens and pests in a shorter time, and a reaction vessel thereof. In this regard, the exterminating device is a device for exterminating pathogens and pests, and this may be simply described as the exterminating device herein. The exterminating device is intended to be a device that exterminates either or both of pathogens and pests.

In order to achieve the above-described objective, a pathogen and pest exterminating device according to a first present invention comprises a reaction vessel, a pair of electrodes, a water supply unit, a gas supply unit, and a power supply unit, and is characterized in that one of the electrodes comprises an insertion part to be inserted into the reaction vessel, the other electrode is arranged in a position that opposes the insertion part, the water supply unit is provided so as to be capable of supplying water to the reaction vessel through the insertion part, the gas supply unit is provided so as to be capable of supplying gas, which will become plasma, to the reaction vessel, the power supply unit is provided so as to be capable of applying voltage between the insertion part and the other electrode such that OH radicals are generated in the reaction vessel to which the water and the gas are supplied, and the insertion part is formed in a shape that restricts, between itself and the other electrode, a flow rate of the water supplied from the water supply unit.

The exterminating device according to the first present invention can efficiently generate OH radicals by introducing the water from the water supply unit to the reaction vessel, supplying the gas, which will become plasma, from the gas supply unit to the reaction vessel, and applying voltage between the insertion part of the one of the electrodes and the other electrode with the power supply unit, thereby causing the gas to discharge in the reaction vessel and the water to evaporate. At this time, since the insertion part is formed in the shape that restricts, between itself and the other electrode, the flow rate of the water supplied from the water supply unit, the time the water stays between the insertion part and the other electrode can be extended, and the evaporation of the water is facilitated. Thus, evaporation quantity of the water can be increased by increasing supply quantity of the water from the water supply unit, and many OH radicals can be generated per unit time. In addition, pathogens and pests can be exterminated by irradiating those OH radicals.

Since the exterminating device according to the first present invention can generate more OH radicals even when power from the power supply unit is the same, it can efficiently exterminate pathogens and pests. In addition, even if power from the power supply unit is increased, generation quantity of the OH radicals can be increased by increasing the supply quantity of the water from the water supply unit even more, and thus pathogens and pests can be exterminated more efficiently. In this manner, the pathogen and pest exterminating device according to the first present invention can efficiently exterminate pathogens and pests in a shorter time.

In the exterminating device according to the first present invention, the insertion part may be formed in any shape as long as that shape restricts the flow rate of the water that is supplied to the inside of the reaction vessel. The insertion part is preferably formed in a coil, waveform, or mesh shape that is made of an elongated metal wire, such that it restricts the flow rate of the water flowing with gravity when being arranged along the vertical direction, for example.

A pathogen and pest exterminating device according to a second present invention comprises a reaction vessel, a pair of electrodes, a water supply unit, a flow rate restricting unit, a gas supply unit, and a power supply unit, and is characterized in that one of the electrodes comprises an insertion part to be inserted into the reaction vessel, the other electrode is arranged in a position that opposes the insertion part, the water supply unit is provided so as to be capable of supplying water to the reaction vessel through the insertion part, the flow rate restricting unit is provided so as to be capable of restricting a flow rate of the water supplied from the water supply unit between the insertion part and the other electrode, the gas supply unit is provided so as to be capable of supplying gas, which will become plasma, to the reaction vessel, and the power supply unit is provided so as to be capable of applying voltage between the insertion part and the other electrode such that OH radicals are generated in the reaction vessel to which the water and the gas are supplied.

The exterminating device according to the second present invention can extend the time the water stays between the insertion part and the other electrode with the flow rate restricting unit. Thus, evaporation quantity of the water can be increased by increasing supply quantity of the water from the water supply unit, and many OH radicals can be generated per unit time. The flow rate restricting unit is not limited, and it may be any means having a configuration that can extend the time the water stays between the insertion part and the other electrode. The exterminating device according to the second present invention can efficiently generate the OH radicals, and can exterminate pathogens and pests in a shorter time, as in the case of the exterminating device according to the first present invention.

In the pathogen and pest exterminating device according to the first and second present inventions, the reaction vessel is formed in a tube shape, wherein the insertion part is inserted from an opening at one end, and the OH radicals are irradiated from an opening at the other end, the insertion part extends along a length direction of the reaction vessel, and the other electrode is provided along a lateral surface of the reaction vessel, in which a length of a portion that opposes the insertion part is preferably from 80 mm to 1000 mm, more preferably longer than 80 mm and 1000 mm or shorter. In this case, the contact area of the water and the insertion part can be increased, and thus the generation quantity of the OH radicals can be further increased. Therefore, pathogens and pests can be exterminated more efficiently in a shorter time. In this case, the reaction vessel may be arranged along the vertical direction, or may be arranged along an oblique direction or the horizontal direction.

The exterminating device according to the first and second present inventions may be configured such that the evaporation rate of the water supplied from the water supply unit in the reaction vessel is preferably 90 μl/min or higher, more preferably 250 μl/min or higher, and even more preferably 1000 μl/min or higher. When the evaporation rate is lower than 90 μl/min, sterilization performance on pathogens and the like may be degraded, and it is not preferable. The evaporation rate is desirably 1 ml/min or lower in view of device cost and performance. Under such condition, pathogens and pests can be exterminated more efficiently in a shorter time.

A pathogen and pest exterminating device according to a third present invention comprises a reaction vessel, a pair of electrodes, a water supply unit, a gas supply unit, and a power supply unit, and is characterized in that one of the electrodes comprises an insertion part to be inserted into the reaction vessel, the other electrode is arranged in a position that opposes the insertion part, the water supply unit is provided so as to be capable of supplying water to the reaction vessel through the insertion part, the gas supply unit is provided so as to be capable of supplying gas, which will become plasma, to the reaction vessel, the power supply unit is provided so as to be capable of applying voltage between the insertion part and the other electrode such that OH radicals are generated in the reaction vessel to which the water and the gas are supplied, and an evaporation rate of the water supplied from the water supply unit in the reaction vessel is 90 μl/min or higher.

The exterminating device according to the third present invention comprises the reaction vessel, the pair of electrodes, the water supply unit, the gas supply unit, and the power supply unit, and it may further comprises a flow rate restricting unit. The exterminating device according to the third present invention can efficiently generate the OH radicals, and can exterminate pathogens and pests, as in the case of the exterminating device according to the first present invention. In the exterminating device according to the third present invention, the evaporate rate of the water in the reaction vessel is preferably in the range of 90 μl/min or higher, wherein more OH radicals can be generated per unit time, and pathogens and pests can be exterminated in a shorter time.

In the exterminating device according to the third present invention, the evaporation rate of the water supplied from the water supply unit in the reaction vessel is more preferably 250 μl/min or higher, and is desired to be 1000 μl/min or higher. When the evaporation rate satisfies the above-described condition, pathogens and pests can be exterminated in a further shorter time.

The exterminating devices according to the first to third present inventions can continuously exterminate pathogens and pests by continuously supplying water from the water supply unit to the inside of the reaction vessel so as to supplement evaporated water. The pathogen and pest exterminating device according to the first to third present inventions can perform sterilization or insect killing on crops, soils, and the like without using agricultural chemicals, or with reduced usage of agricultural chemicals, when being used in the field of agriculture.

In the exterminating devices according to the first to third present inventions, the gas supplied from the gas supply unit can be any gas as long as it will become plasma, and is formed of, for example, any one of air, nitrogen, oxygen, helium, and argon, or a mixture of those gases. The supply quantity of the gas is preferably small, and is preferably, for example, 1 slm (L/min) to 20 slm (L/min) at room temperature (e.g., in the range of 15 to 30° C.). The water supplied from the water supply unit can be supplied in any form, and it is for example, water droplets or water mists. The evaporation rate (or supply quantity) of the water is preferably 90 μl/min or higher, more preferably 250 μl/min or higher, and even more preferably 1000 μl/min or higher.

The power supply unit is preferably pulse power supply, and it may be AC power supply. The exterminating devices according to the first to third present inventions may comprise a cooling means that is configured to maintain the plasma including the generated OH radicals at a predetermined temperature or lower. In this case, since ozone is less likely to be generated if the generated plasma has a high temperature, the generation of ozone can be suppressed by allowing the plasma to rise to a certain temperature, and it is also possible to suppress wear of electrodes, and influences on irradiated objects such as plants, due to a high temperature. The irradiation time of the plasma for exterminating pathogens and pests is preferably within 100 seconds, and more preferably within 20 seconds.

The exterminating devices according to the first to third present inventions may be used on any objects among those that will receive, or have received, some kinds of damages, due to pathogens and pests. For example, in the field of agriculture, the exterminating device is preferably used on plants, soils, or liquid fertilizers. In this regard, pathogens are organisms that become causes of mainly plant diseases, and they are for example, pathogenic bacteria such as filamentous bacteria (mainly, molds) and germs (bacteria), and viruses. The pathogenic bacteria are, for example, rice blast, wheat powdery mildew, soybean purpura, strawberry gray mold disease, cucumber gray mold disease, tomato gray mold disease, lily leaf blight, cucumber powdery mildew, strawberry powdery mildew, tomato leaf mold disease, onion rust disease, *chrysanthemum* white rust disease, green onion black spot disease, apple spot deciduous disease, cucumber brown spot disease, crown daisy anthrax, parsley leaf blight, apple brown spot disease and bakanae disease. The pests are pests that harm mainly plants, and they are for example, ticks and aphids.

A reaction vessel of a pathogen and pest exterminating device according to the present invention comprises an opening part for supplying each of water and gas, which will become plasma, to the inside, and a pair of electrodes, and is characterized in that one of the electrodes comprises an insertion part to be inserted into the reaction vessel from the opening part, the other electrode is arranged in a position that opposes the insertion part, and the insertion part is formed in a shape that restricts, between itself and the other electrode, a flow rate of the water supplied from the opening part. Furthermore, the reaction vessel comprises an opening part for irradiating the plasma including generated OH radicals to an irradiated object, and is preferably in a tube-shaped form.

The reaction vessel of a pathogen and pest exterminating device according to the present invention is suitably used as the reaction vessel of the exterminating devices according to the first to third present inventions. In the reaction vessel of a pathogen and pest exterminating device according to the present invention, the insertion part is formed in a shape that restricts a flow rate of water, and is preferably formed in, for example, a coil, waveform, or mesh shape.

Effect of the Invention

According to the present invention, a pathogen and pest exterminating device that can efficiently exterminate pathogens and pests in a shorter time, and a reaction vessel thereof, can be provided.

BRIEF DESCRIPTION OF THE DRAWINGS

FIG. 2(*b*) is an example of the reaction vessel formed in a helical shape; and FIGS. 2(*c*) to (*e*) are examples of an enlarged view of the reaction vessel.

DETAILED DESCRIPTION OF THE INVENTION

Hereinafter, an embodiment of the present invention will be described based on the drawings.

Figure 1:
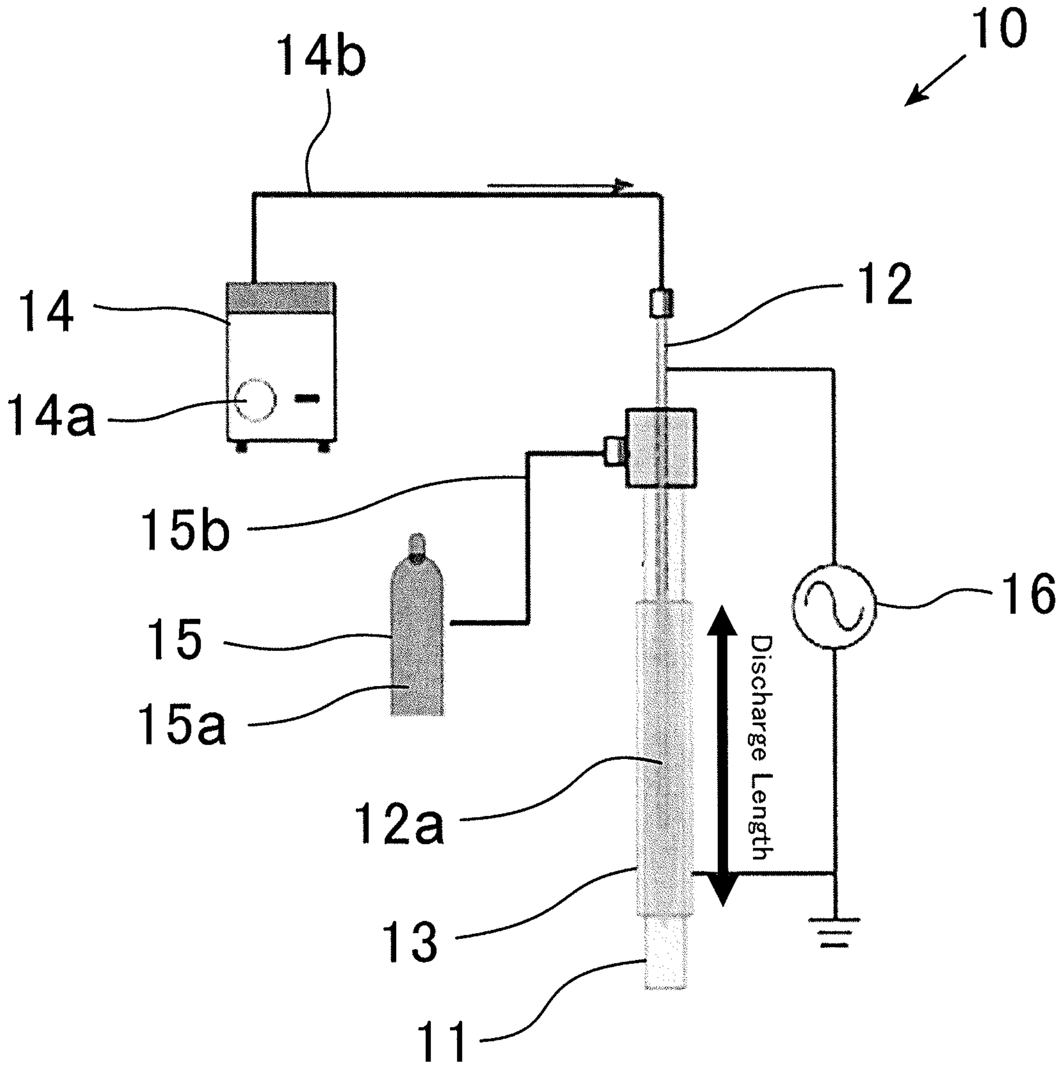
FIG. 1 is an example of a side view showing a pathogen and pest exterminating device according to an embodiment of the present invention.

FIG. 1 shows a pathogen and pest exterminating device according to an embodiment of the present invention.

As shown in FIG. 1, a pathogen and pest exterminating device 10 includes a reaction vessel 11, one electrode 12, other electrode 13, a water supply unit 14, a gas supply unit 15, and a power supply unit 16.

Figure 2:
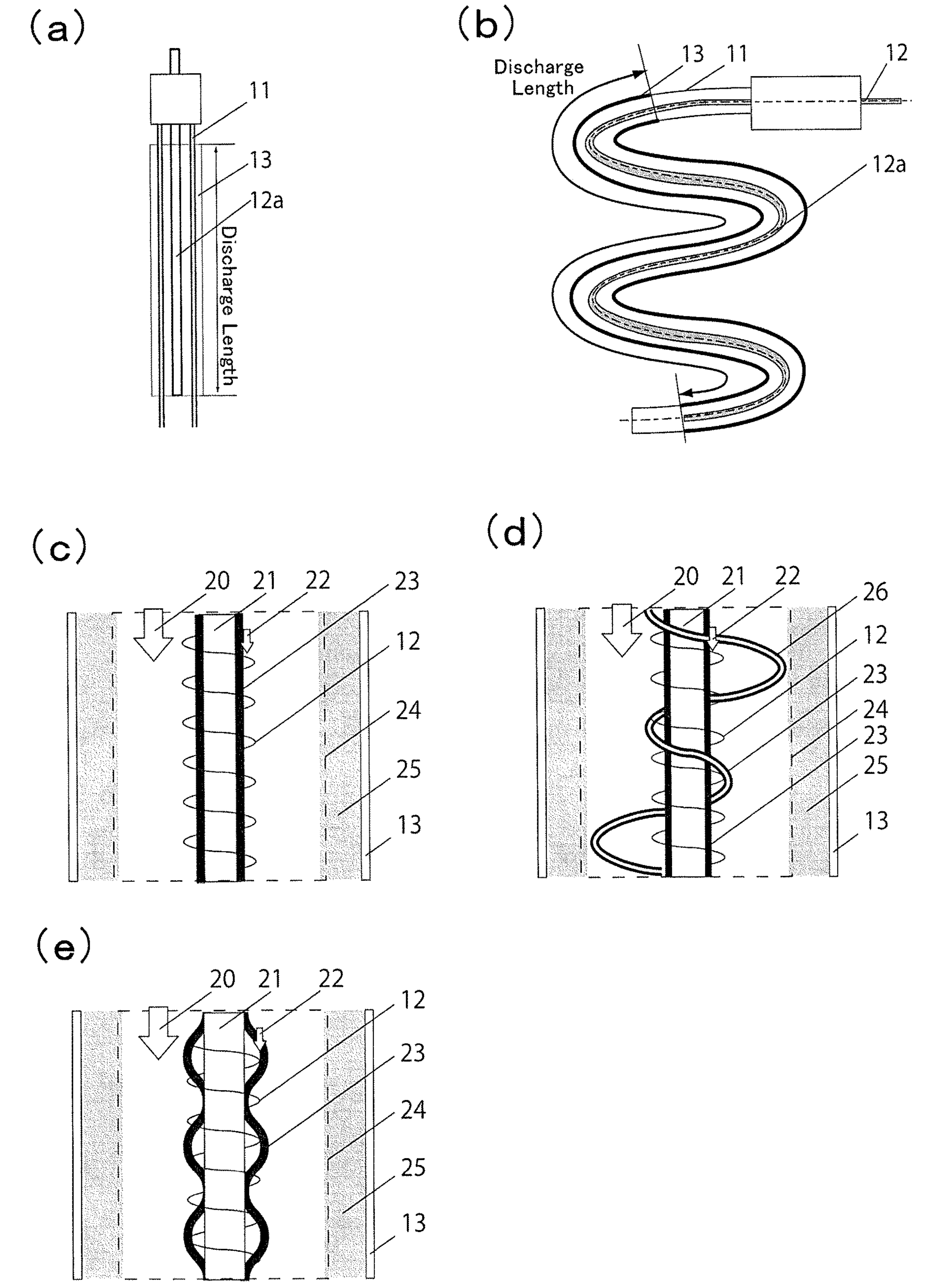
FIG. 2(*a*) is an example of an enlarged view of a reaction vessel of the exterminating device shown in FIG. 1.

FIG. 2(*a*) shows an enlarged view of the reaction vessel 11 used for the pathogen and pest exterminating device according to the embodiment of the present invention. The reaction vessel 11 is a vessel made of a glass such as quartz glass or an insulating material such as resin, and it is formed in an elongated tube shape. The reaction vessel 11 is arranged so as to allow utilization in an optional length in the vertical direction. In the examples shown in FIG. 1 and FIG. 2(*a*), the reaction vessel 11 can be set to a desired length and an optional tube inner/outer diameter. For example, the outer diameter can be selected from about 5 to 10 mm, and the inner diameter can be selected from a size that is about 1 to 5 mm, which is a range smaller than the outer diameter. The length can be selected from 80 to 1000 mm.

The reaction vessel 11 is manufactured to have a compactly formed structure of a linear, coil (helical), or quasi-polygonal shape, as a shape to be arranged so as to allow utilization in an optional length in the vertical direction. FIG. 2(*a*) is a structural drawing in which the reaction vessel 11 is manufactured in a linear shape, and FIG. 2(*b*) represents a structural drawing of a coil shape.

The one electrode 12 includes a structure in which an elongated metal wire is formed within the reaction vessel 11, in a shape that can restrict a flow rate of the water supplied from the water supply unit. For example, the one electrode 12 is formed in a coil (FIG. 2(*c*) to FIG. 2(*e*)), waveform, or mesh shape. In this regard, a structure in which a flow rate of water is not restricted, which is a comparison target, is a structure that is formed by inserting, along a flow rate vector of water, the one electrode in the same vector direction. More specifically, the one electrode in this case has a structure that is formed by inserting the elongated metal wire into the reaction vessel along the flow rate vector of water.

With regard to the one electrode 12 of the present invention, for example, a core material such as that made of quartz is inserted into the coil. The one electrode 12 is arranged such that its front-end part is inserted into the reaction vessel 11 from an opening at an upper end thereof, and its rear-end part is projected from the opening at the upper end of the reaction vessel 11. In the example shown in FIG. 1, the one electrode 12 is made of a tungsten wire having a diameter of 0.01 to 0.5 mm, and is formed in a coil shape having a diameter of 0.5 to 5 mm. The one electrode 12 may be made of copper, and it may be made of any metal material having high corrosion resistance that can be formed into an electrode.

The other electrode 13 is preferably formed in a thin sheet form, and for example, it is made of a copper foil and is attached to the reaction vessel 11 by being wound once around the lateral surface thereof. The other electrode 13 is attached along a predetermined range in the vertical direction of the reaction vessel 11. The other electrode 13 is arranged so as to oppose the one electrode 12, which is inserted into the reaction vessel 11. In the example shown in FIG. 1, the other electrode 13 has a length of from 80 mm to 1000 mm along the vertical direction of the reaction vessel 11. The other electrode 13 is preferably in the range of over 80 mm and 1000 mm or shorter, and is further preferably in the range of 90 mm to 1000 mm. In the one electrode 12, a portion opposing the other electrode 13 forms an insertion part 12*a*.

The water supply unit 14 includes a water pump 14*a* for supplying water, and a water supply tube 14*b* for flowing water from the water pump 14*a*. The water pump 14*a* is capable of adjusting the amount of water to be flowed into the water supply tube 14*b*. The water supply tube 14*b* is connected to the upper end of the one electrode 12 so as to be capable of supplying water droplets into the coil of the one electrode 12. In this manner, the water supply unit 14 is capable of supplying water into the reaction vessel 11 through the insertion part 12*a* of the one electrode 12.

The gas supply unit 15 includes a gas cylinder 15*a* that is filled with gas, which will become plasma, and a gas supply tube 15*b* for flowing the gas from the gas cylinder 15*a*. The gas supply unit 15 is capable of adjusting the amount of gas to be flowed into the gas supply tube 15*b*. The gas can be any gas that will become plasma such as air, nitrogen, oxygen, helium, and argon. In the example shown in FIG. 1, air is preferably used as the gas. The gas supply tube 15*b* is connected to the upper end of the reaction vessel 11 so as to be capable of supplying the gas into the reaction vessel 11 from the opening at the upper end.

The power supply unit 16 is formed of DC power supply or AC power supply, and is provided by being connected to the one electrode 12 and the other electrode 13 so as to be capable of applying voltage between the insertion part 12*a* of the one electrode 12 and the other electrode 13. In this manner, the power supply unit 16 generates OH radicals inside the reaction vessel 11 by discharging the gas in the inside of the reaction vessel 11 to which the water from the water supply unit 14 and the gas from the gas supply unit 15 are supplied. The power supply unit 16 may be formed of pulse power supply.

The exterminating device 10 of the present invention is configured such that the one electrode 12 is formed in a coil, waveform, or mesh shape, and a flow rate when the water supplied from the water supply unit 14 downwardly flows through the insertion part 12*a* can be restricted between the insertion part 12*a* and the other electrode 13. The exterminating device 10 is configured such that the plasma including the OH radicals generated within the reaction vessel 11 is discharged from an opening at a lower end of the reaction vessel 11, in accordance with the flow of the gas supplied from the gas supply unit 15.

The following describes the mechanism.

The pathogen and pest exterminating device 10 can efficiently generate the OH radicals by introducing the water from the water supply unit 14 into the reaction vessel 11, supplying the gas, which will become plasma, from the gas supply unit 15 to the reaction vessel 11, and applying voltage between the insertion part 12*a* of the one electrode 12 and the other electrode 13 with the power supply unit 16, thereby causing the gas to discharge in the reaction vessel 11 and the water to evaporate. At this time, since the insertion part 12*a* is formed in a coil shape, and the flow rate of the water supplied from the water supply unit 14 can be restricted between the insertion part 12*a* and the other electrode 13, the time the water stays between the insertion part 12*a* and the other electrode 13 can be extended, and the evaporation of the water is facilitated. Accordingly, the evaporation quantity of the water can be increased by increasing the supply quantity of the water from the water supply unit 14, and more OH radicals can be generated per unit time. Since the contact area of the water and the insertion part 12*a* is large, the generation quantity of the OH radicals can be further increased. By irradiating those OH radicals to an object from the opening at the lower end of the reaction vessel 11, pathogens and pests can be exterminated.

The pathogen and pest exterminating device 10 can generate more OH radicals as compared to a comparative example, which will be described later, even if power from the power supply unit 16 is the same. Thus, pathogens and pests can be efficiently exterminated. Even if power from the power supply unit 16 is increased, the generation quantity of the OH radicals can be increased by increasing the supply quantity of the water from the water supply unit 14 even more, and thus pathogens and pests can be exterminated more efficiently. In this manner, the pathogen and pest exterminating device 10 can efficiently exterminate pathogens and pests in a shorter time.

The pathogen and pest exterminating device 10 can continuously exterminate pathogens and pests by continuously supplying the water from the water supply unit 14 to the inside of the reaction vessel 11 so as to supplement evaporated water. The pathogen and pest exterminating device 10 can perform sterilization or insect killing on crops, soils, liquid fertilizers, and the like without using agricultural chemicals, when being used in the field of agriculture.

The pathogen and pest exterminating device 10 may include a flow rate restricting unit that is provided so as to restrict the flow rate of the water supplied from the water supply unit 14 between the insertion part 12*a* and the other electrode 13. In this case, the time the water stays between the insertion part 12*a* and the other electrode 13 can be extended even if the one electrode 12 is not formed in a coil shape or the like. Thus, the evaporation quantity of the water can be increased by increasing the supply quantity of the water from the water supply unit 14, and more OH radicals can be generated per unit time.

For example, the pathogen and pest exterminating device 10 may include the configurations shown in FIGS. 2(*c*) to (*e*). In FIGS. 2(*c*) to (*e*), reference sign 20 denotes a gas flow, reference sign 21 denotes an electrode guide (core material) of the one electrode, reference sign 22 denotes a water flow on an electrode guide surface of the one electrode, reference sign 23 denotes a water flow wet surface, reference sign 24 denotes a discharge unit, reference sign 25 denotes a reaction vessel wall, and reference sign 26 denotes a water flow restrictor. Thick lines indicate places where the water flow is present. As shown in FIG. 2(*c*), a relatively simple configuration in which the one electrode 12 having a coil shape is wound around the core material 21, may be used. As shown in FIG. 2(*d*), the water flow restrictor 26, which is provided so as to be capable of restricting the flow rate of the water supplied from the water supply unit 14 between the insertion part 12*a* and the other electrode 13, may be included as the flow rate restricting unit. In this example, the water flow restrictor 26 is formed in a coil shape having a larger diameter than the one electrode 12, and is wound around the core material 21. The water is flowed not only along the surface of the core material 21, but also along the water flow restrictor 26. In this manner, the time the water stays between the insertion part 12*a* and the other electrode 13 can be extended with both the insertion part 12*a* and the water flow restrictor 26. As shown in FIG. 2(*e*), concavities and convexities that are repeated along the length direction may be provided on the surface of the core material 21 to be used as the flow rate restricting unit. The time the water stays between the insertion part 12*a* and the other electrode 13 can also be extended in this case with both the insertion part 12*a* and the concavities and convexities of the core material 21.

Hereinafter, the present invention will be specifically described with examples. However, the technical scope of the present invention will not be limited in any way by those descriptions.

Example 1

In order to examine a sterilization effect exerted by the exterminating device 10 shown in FIG. 1, an experiment was conducted by using *Colletotrichum gloeosporioides* (C.glo), which is a type of *Glomerella cingulata* in the field of agriculture. Since C.glo conidia germinate in water, in the experiment, plasma was irradiated toward a suspension to which C.glo conidia before germination were added, and the germination rate of C.glo conidia after a passage of a predetermined time was examined. 5 μl of distilled water to which C.glo conidia before germination were added at a concentration of $1\text{-}2\times10^{6}$ conidia/ml, was used as the suspension. The distance between the lower end edge of the reaction vessel 11 and the surface of the suspension was set to 10 cm. The elapsed time until the examination of the germination rate after the irradiation was set to a time until the germination rate of a prepared control suspension, to which plasma was not irradiated, reaches a predetermined value between 80 to 100% (about 6 to 12 hours).

Figure 3:
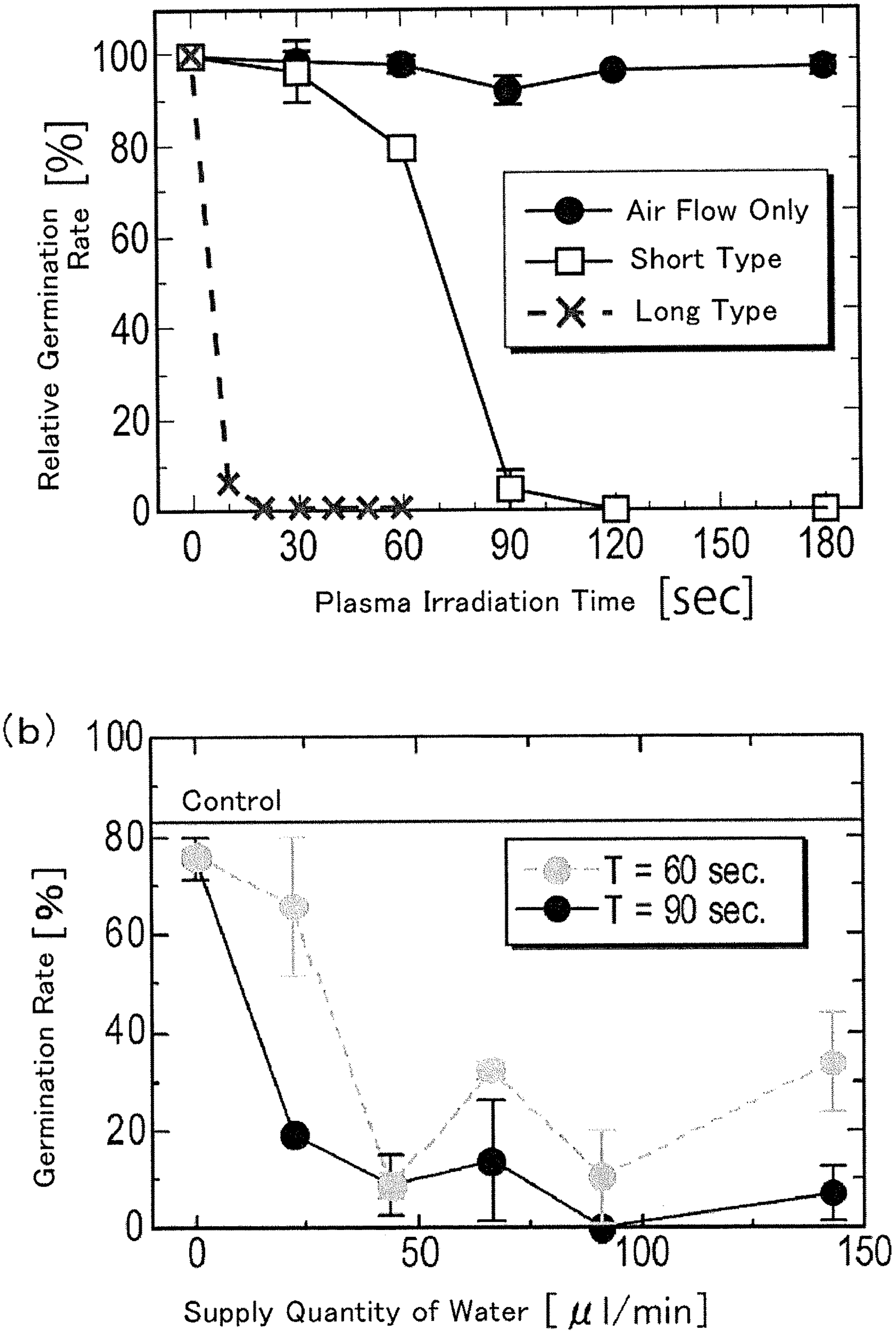
FIG. 3(*a*) represents a graph indicating a relation between a plasma irradiation time and a relative germination rate of C.glo conidia when using the exterminating device shown in FIG. 1, and FIG. 3(*b*) represents a graph indicating a relation between supply quantity of water and a germination rate of C.glo conidia.

First, the experiment was conducted by using the exterminating device (short type) 10 that was manufactured such that the length of the other electrode 13 will be 92 mm, i.e., the length of the portion where the insertion part 12*a* and the other electrode 13 oppose each other (discharge length: $L_{dis}$) will be 92 mm. The one electrode 12 is stored up to the insertion part 12*a*, and it is formed in a coil shape as shown in FIG. 2(*c*). In this regard, in the present specification, the exterminating device 10 having a discharge length of the above-described length may be described as the short type. The experiment was conducted by setting the supply quantity of the water from the water supply unit 14 to 93 μl/min, and the supply quantity of the air from the gas supply unit 15 to 16 slm (L/min). In the experiment, the germination rate of C.glo conidia at the times when the irradiation times of the plasma were 0, 30, 60, 90, 120, and 180 seconds, was examined. The results are shown in FIG. 3(*a*). For comparison, the result of a case in which only the air was supplied to the inside of the reaction vessel 11, and the water was not supplied, is also shown.

As shown in FIG. 3(*a*), when only the air was supplied, the germination rate of C.glo conidia did not decrease even if the irradiation time of the plasma was extended, and a sterilization effect was hardly recognized. In contrast, when water was also supplied in addition to the air, it was confirmed that the germination rate of C.glo conidia rapidly decreased to 1/10 or lower, and the sterilization effect became remarkably high, once the irradiation time of the plasma exceeded 90 seconds. In this manner, even if power from the power supply unit 16 is the same, more OH radicals can be generated by supplying the water, and pathogens and pests can be efficiently exterminated.

Next, by using the same pathogen and pest exterminating device 10, an experiment was conducted by setting the supply quantity of the air from the gas supply unit 15 to 16 slm (L/min), and the irradiation time of the plasma to 60 seconds or 90 seconds. The experiment examined the germination rate of C.glo conidia when the supply quantity of the water from the water supply unit 14 was changed within the range of 0 to 140 μl/min. The results are shown in FIG. 3(*b*).

As shown in FIG. 3(*b*), when the irradiation time of the plasma was 60 seconds, it was confirmed that the germination rate of C.glo conidia decreased to about 1/2 to 1/5 of the control, and the sterilization effect became higher, when the supply quantity of the water was set to about 40 μl/min or more. When the irradiation time of the plasma was 90 seconds, it was confirmed that the germination rate of C.glo conidia decreased to 1/4 or lower when the supply quantity of the water was set to about 20 μl/min or more, particularly to 1/10 or lower with about 90 μl/min or more, and the sterilization effect became remarkably higher. When the supply quantity of the water was increased, it was confirmed that the maximum quantity was 140 μl/min, and even if the water was further supplied, the germination rate did not decrease, and the water dropped from the lower end of the reaction vessel 11.

Example 2

An experiment was conducted by using the pathogen and pest exterminating device (long type) 10, wherein the length of the other electrode 13 is set to 500 mm, i.e., the length of the portion in which the insertion part 12*a* and the other electrode 13 oppose each other (discharge length: $L_{dis}$) is set to 500 mm. The one electrode 12 is formed in a coil shape as shown in FIG. 2(*c*). In this regard, in the present specification, the exterminating device 10 having a discharge length of the above-described length may be described as the long type. The experiment was conducted by setting the supply quantity of the water from the water supply unit 14 to 1200 μl/min, and the supply quantity of the air from the gas supply unit 15 to 16 slm (L/min). The experiment examined the germination rate of C.glo conidia when the irradiation times of the plasma were 0, 10, 20, 30, 40, 50, and 60 seconds. The results are shown in FIG. 3(*a*).

As shown in FIG. 3(*a*), it was confirmed that when the irradiation time of the plasma exceeded 10 seconds, the germination rate of C.glo conidia rapidly decreased to 1/10 or lower, and the sterilization effects become remarkably high particularly when exceeding 20 seconds, where the germination rate became almost zero.

Example 3

An experiment was conducted to examine a sterilization effect when the supply quantity of the air was made small, by using the exterminating device 10 of the short type with the discharge length $L_{dis}$ of 92 mm, and of the long type with the discharge length $L_{dis}$ of 500 mm. In the case of the short type, the germination rate of C.glo conidia was examined by setting the supply quantity of the air from the gas supply unit 15 to 8 slm (L/min), the irradiation time of the plasma to 90 seconds, and the supply quantity of the water from the water supply unit 14 to 0-220 μl/min. In the case of the long type, the germination rate of C.glo conidia was examined by setting the supply quantity of the air from the gas supply unit 15 to 8 slm (L/min) or 10 slm (L/min), the irradiation time of the plasma to 20 seconds, and the supply quantity of the water from the water supply unit 14 to 0-1200 μl/min. Those results are shown in FIGS. 4(*a*) and (*b*).

Figure 4:
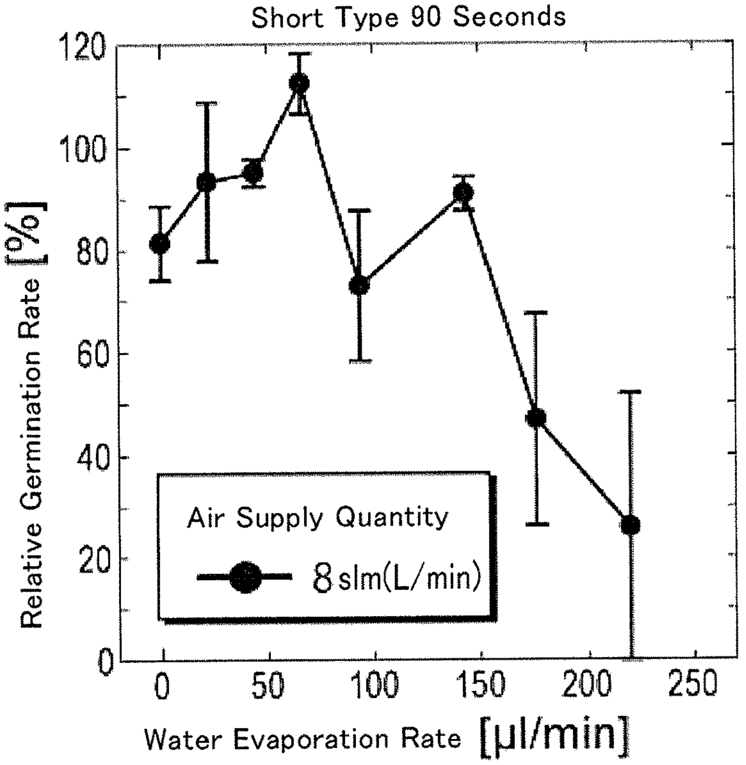
FIG. 4(*a*) represents a graph indicating a relation between an evaporation rate of water and a relative germination rate of C.glo conidia when a short type device of the exterminating device shown in FIG. 1 is used, and FIG. 4(*b*) represents a graph indicating an equivalent relation when a long type device is used.
Figure 4:
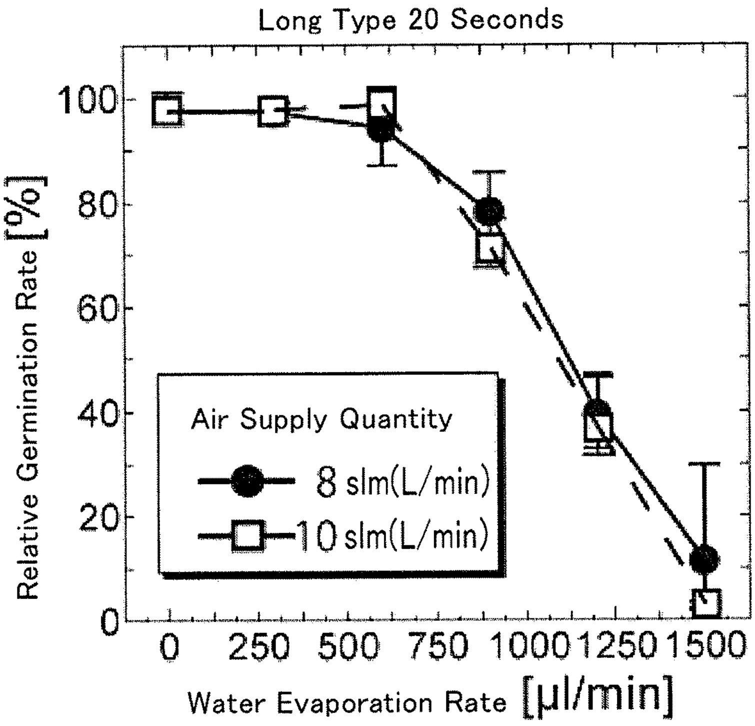

As shown in FIG. 4(*a*), in the case of the short type, it was confirmed that the germination rate of C.glo conidia decreased to about 1/4 when the supply quantity of the water was set to 220 μl/min. It was confirmed that the sterilization effect will be lowered if the supply quantity of the air is decreased as compared to when the supply quantity of the air is 16 slm (L/min) as shown in FIG. 3(*a*).

As shown in FIG. 4(*b*), in the case of the long type, it was confirmed that the germination rate of C.glo conidia decreased to about 1/10 or lower when the supply quantity of the water was set to 1200 μl/min. It was confirmed that a sufficient sterilization effect can be obtained with the irradiation time of the plasma of 20 seconds, even if the supply quantity of the air is decreased as compared to when the supply quantity of the air is 16 slm (L/min) as shown in FIG. 3(*a*).

Example 4

An experiment was conducted to examine the concentration of ozone generated by the plasma irradiation, by using the exterminating device 10 of the short type with the discharge length $L_{dis}$ of 92 mm, and of the long type with the discharge length $L_{dis}$ of 500 mm. The ozone concentration in the irradiated plasma was measured in the cases where there is no supply of water from the water supply unit 14, and where the supply quantity of the water is 93.5 μl/min, while setting the supply quantity of the air from the gas supply unit 15 to 8-16 slm (L/min). The results are shown in FIG. 5.

Figure 5:
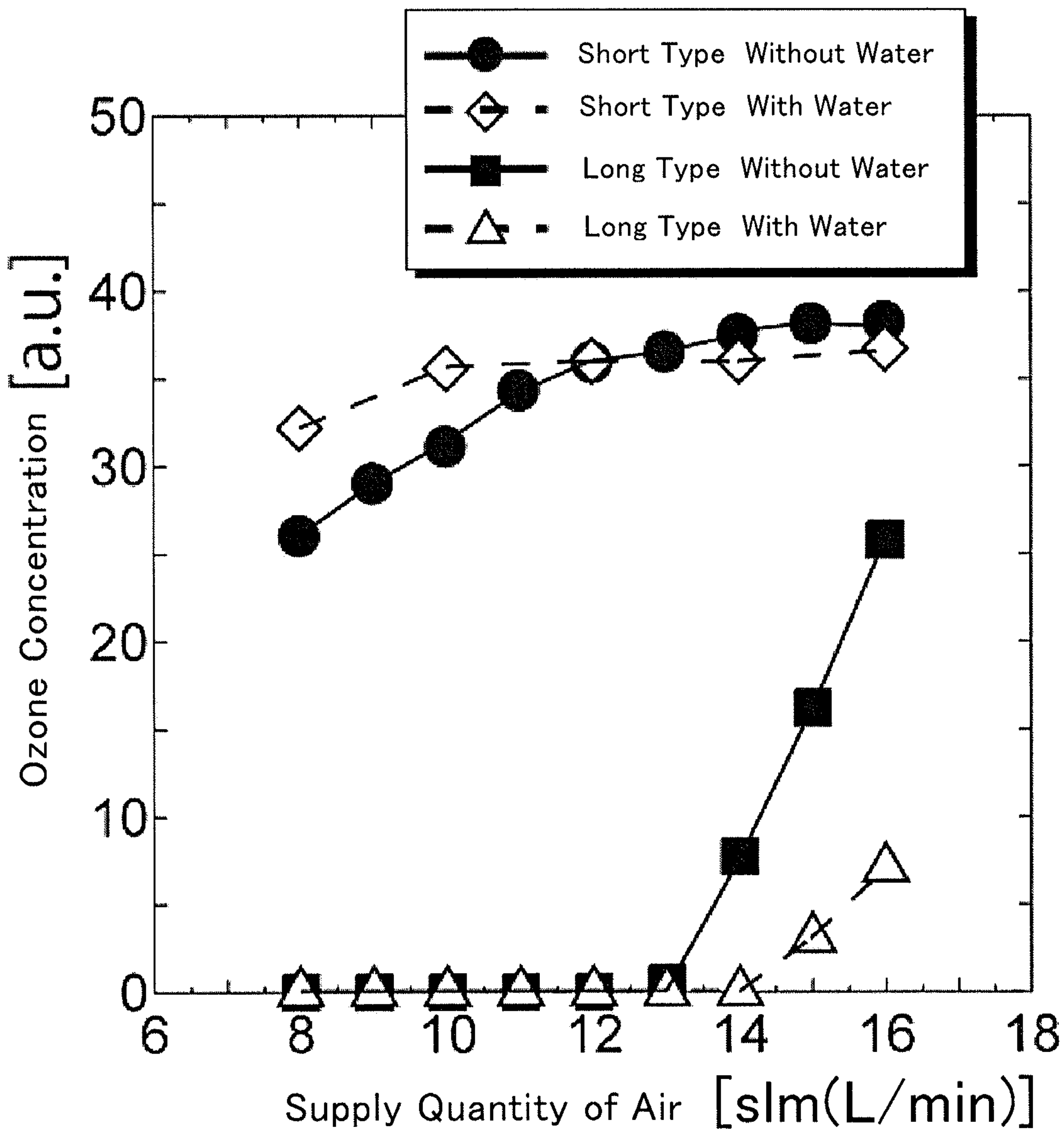
FIG. 5 represents a graph indicating a relation between supply quantity of air and a concentration of generated ozone, which indicates an effect of supplying water, when using the short type and long type exterminating devices.

As shown in FIG. 5, in the case of the short type, it was confirmed that the ozone concentration is almost unaffected by the presence or absence of water supply. In the case of the long type, it was confirmed that the ozone concentration was lower as compared to the short type, and when the supply quantity of the air was 13 slm (L/min) or smaller, the ozone concentration was almost zero regardless of the presence or absence of water supply. It was also confirmed that when the supply quantity of the air was greater than 13 slm (L/min), the ozone concentration became lower when the water was supplied, as compared to when the water was not supplied.

With regard to the exterminating devices 10 of the short type and the long type, the applied voltage, the frequency, the discharge power, and the like of the power supply unit 16 during an operation were put together, and shown in Table 1. Since the discharge becomes unstable due to a voltage drop if the discharge length is made long, the power supply frequency was made high as shown in Table 1 for supplement. As shown in Table 1, when the discharge length was made longer, the discharge power was increased about threefold, and the maximum water supply quantity was increased about eightfold, which is even greater. From this point, with each of the exterminating devices 10, even if power from the power supply unit 16 was increased, the generation quantity of the OH radicals can be increased by increasing the supply quantity of the water even more. Thus, power consumption can be rather reduced by shortening the irradiation time for sterilization. From this point, each of the exterminating devices 10 is recognized as being able to perform extermination of pathogens and pests more efficiently, as compared to a conventionally known pathogen and pest exterminating device (for example, Patent Literature 1).

TABLE 1

| | Short type | Long type |
|---|---|---|
| Full length (mm) | 150 | 700 |
| Discharge length (mm) | 92 | 500 |
| Internal electrode structure | Coil type | Coil type |
| Applied voltage (kV) | 20 | 14 |
| Frequency (kHz) | 8.3 | 11 |
| Irradiation time: $T_i$ (sec) | 0-180 | |
| Operating air flow rate [slm (L/min)] | 4-20 | 8-20 |
| Discharge power (W) | 40 | 130 |
| Maximum water introducing amount (μl/min) | 220 | 1700 |

Comparative Example

A pathogen and pest exterminating device was manufactured with the same process as Example 1, except that the one electrode 12 had a structure in which an elongated metal wire was inserted along the flow rate vector of the water, into the reaction vessel in the same vector direction, while maintaining its linear shape (a structure in which the insertion part 12*a* was not configured to restrict the flow rate, and a structure in which a flow rate restricting unit was not provided within the reaction vessel), which is an arrangement that does not disturb the flow rate of the water. That is, the one electrode 12 had a structure in which an elongated metal wire was inserted along the flow rate vector of the water, into the reaction vessel in the same vector direction, while maintaining its linear shape, which is an arrangement that does not disturb the flow rate of the water. As a result, the exterminating device having the discharge length $L_{dis}$ of 80 mm was achieved.

When the irradiation of the plasma was attempted by setting the supply quantity of the air from the gas supply unit 15 to 8 slm (L/min), and the supply quantity of the water from the water supply unit 14 to 0-220 μl/min, the observed result was such that the water was discharged for not being able to evaporate well, when the evaporation rate of the water exceeded about 100 μl/min. It was confirmed that, in order to irradiate the plasma for exterminating pathogens and pests by utilizing the pathogen and pest exterminating device of the present invention, the insertion part 12*a* must have a configuration that restricts the flow rate, or a flow rate restricting unit must be formed within the reaction vessel.

Example 5

By using the exterminating device 10 of the long type having the discharge length $L_{dis}$ of 500 mm, an experiment was conducted to measure the quantity of active species that are generated by the plasma irradiation when the supply quantity of the air and the supply quantity of the water were changed. As shown in FIG. 2(*d*), the exterminating device 10 used in the experiment had a configuration in which the one electrode 12 is formed in a coil shape, and the water flow restrictor 26 is included. Nitric acid, which is represented by HOONO, and the like can be considered as active species having sterilization action such as germination inhibition. However, since these active species have short lives, and are difficult to be detected, in the experiment, measurements were made on nitrate ions ($NO_3^-$), nitrite ions ($NO_2$), and hydrogen peroxide ($H_2O_2$), which generate those active species by being bound.

In the experiment, the supply quantity of the air was set to 8 slm or 10 slm, and the supply quantity of the water was changed in the range of 0 to 1500 μl/min. The experiment was conducted as follows, for each condition of air supply quantity and water supply quantity. First, active gas that includes active species generated within the reaction vessel 11 by the plasma irradiation, and that is injected from the opening at the lower end of the reaction vessel 11, was sucked into a water circulation device for bubbling with circulating water, so as to dissolve components of the active gas in the circulating water. During the plasma irradiation, sampling of the circulating water was continuously performed, and at the time of the sampling, nitrate ions ($NO_3^-$) were measured by ultraviolet absorption spectrometry. The concentrations of nitrite ions ($NO_2^-$) and hydrogen peroxide ($H_2O_2$) of the sampled circulating water were quantitatively evaluated with "PACKTEST" manufactured by Kyoritsu Chemical-Check Lab., Corp.

In this regard, in order to suppress chemical reactions in the circulating water, and maintain pH of the circulating water higher than 3, the sampling was performed for 1 minute from the start of the plasma irradiation. The liquid quantity of the circulating water was set to 80 ml. The suction position of the water circulation device was set to a position 10 cm downstream of the lower end edge of the reaction vessel 11. From the measured concentrations of the respective active species in nitrate ions, nitrite ions, and hydrogen peroxide, the liquid quantity of the circulating water, and the irradiation time of the plasma, the fluxes (Molecular fluxes) of the respective active species were obtained with concentration×liquid quantity/irradiation time.

Figure 6:
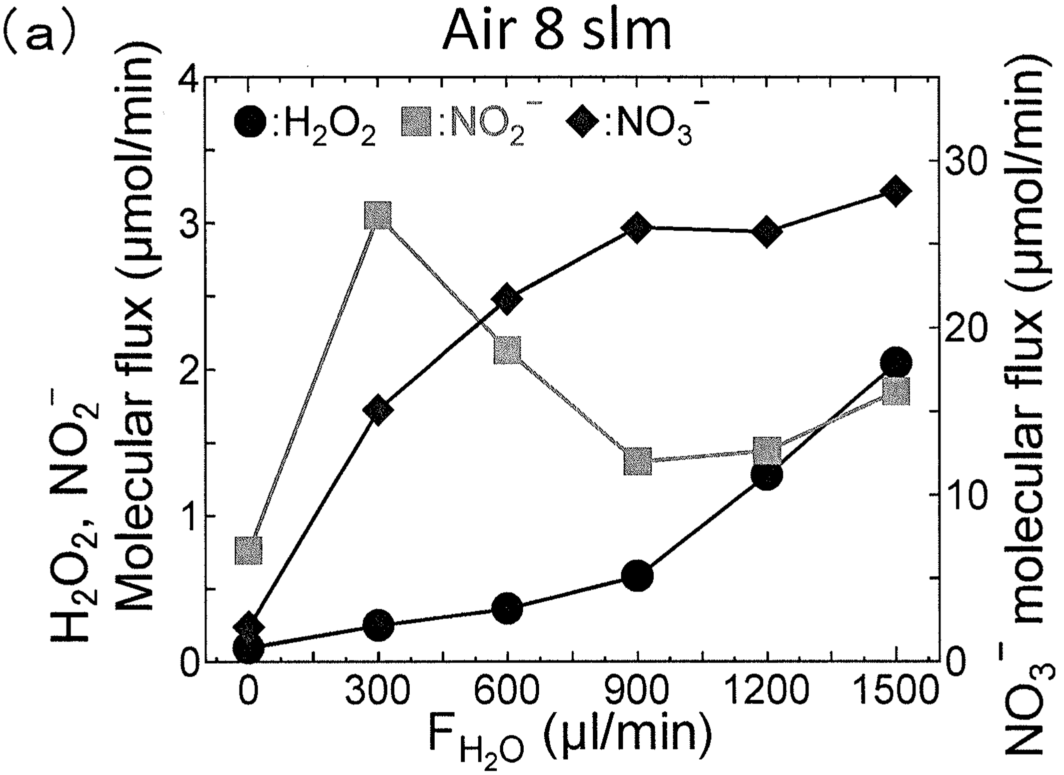
FIG. 6 is a graph indicating a change in fluxes (Molecular fluxes) of nitrate ions ($NO_3^-$), nitrite ions ($NO_2^-$), and hydrogen peroxide ($H_2O_2$) with respect to supply quantity of water ($F_{H2O}$) at the times of (a) supply quantity of air (Air) being 8 slm, and (b) supply quantity of air (Air) being 10 slm, when the long type device of the exterminating device shown in FIG. 1 is used.
Figure 6:
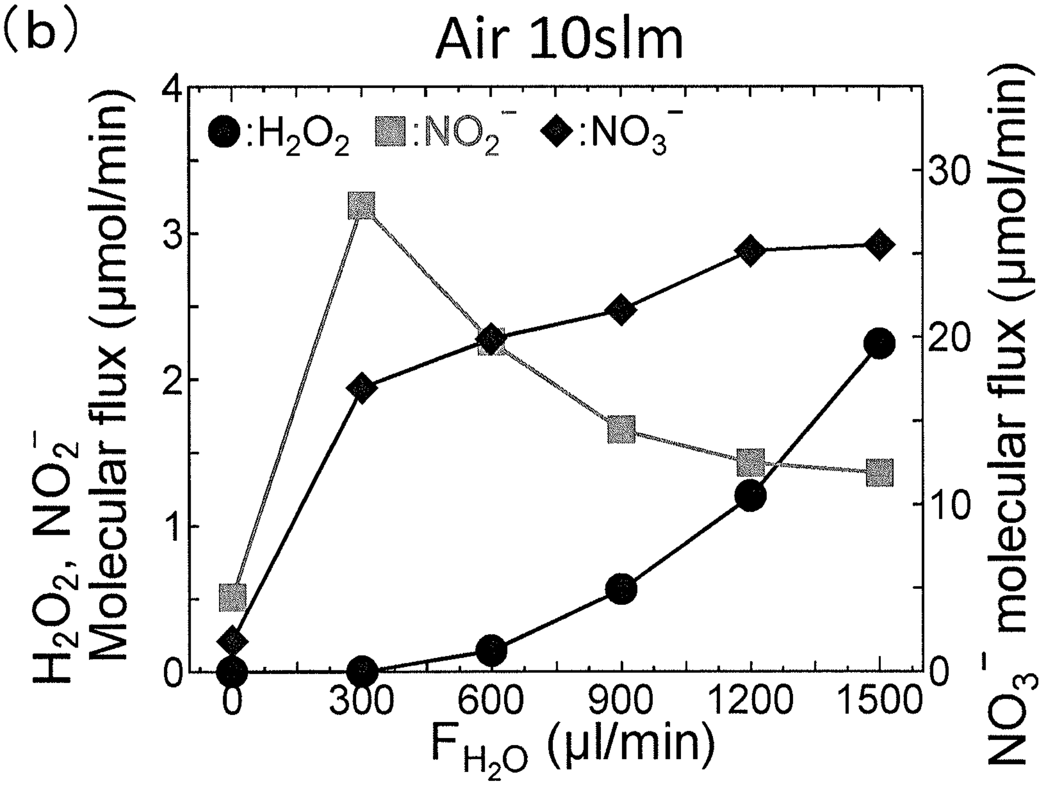

The fluxes of the respective active species obtained for each condition of air supply quantity and water supply quantity were put together, and shown in FIG. 6. As shown in FIGS. 6(*a*) and (*b*), it was confirmed that the amounts (fluxes) of hydrogen peroxide and nitrate ions increased in accordance with the increase in the supply quantity of the water ($F_{H2O}$). It was confirmed that the amount of nitrite ions was the largest when the supply quantity of the water was 300 μl/min, and was decreased around that quantity.

REFERENCE SIGNS LIST

10: pathogen and pest exterminating device
11: reaction vessel
12: one electrode
12*a*: insertion part
13: other electrode
14: water supply unit
14*a*: water pump
14*b*: water supply tube
15: gas supply unit
15*a*: gas cylinder
15*b*: gas supply tube
16: power supply unit
20: gas flow
21: electrode guide (core material) of one electrode
22: water flow on electrode guide surface of one electrode
23: water flow wet surface
24: discharge unit
25: reaction vessel wall
26: water flow restrictor

What is claimed is:

1. A pathogen and pest exterminating device, comprising a reaction vessel, a pair of electrodes, a water supply unit, a gas supply unit, and a power supply unit, wherein
one of the electrodes comprises an insertion part to be inserted into the reaction vessel,
the other electrode is arranged at a position that opposes the insertion part,
the water supply unit is provided so as to be capable of supplying water to the reaction vessel through the insertion part,
the gas supply unit is provided so as to be capable of supplying gas, which will become plasma, to the reaction vessel,
the power supply unit is provided so as to be capable of applying voltage between the insertion part and the other electrode such that OH radicals are generated in the reaction vessel to which the water and the gas are supplied, and
the insertion part is formed in a shape that restricts, between itself and the other electrode, a flow rate of the water supplied from the water supply unit.

2. The pathogen and pest exterminating device of claim 1, wherein the insertion part is formed in a coil, waveform, or mesh shape.

3. A pathogen and pest exterminating device, comprising a reaction vessel, a pair of electrodes, a water supply unit, a flow rate restricting unit, a gas supply unit, and a power supply unit, wherein
one of the electrodes comprises an insertion part to be inserted into the reaction vessel,
the other electrode is arranged in a position that opposes the insertion part,
the water supply unit is provided so as to be capable of supplying water to the reaction vessel through the insertion part,
the flow rate restricting unit is provided so as to be capable of restricting a flow rate of the water supplied from the water supply unit, between the insertion part and the other electrode,
the gas supply unit is provided so as to be capable of supplying gas, which will become plasma, to the reaction vessel, and
the power supply unit is provided so as to be capable of applying voltage between the insertion part and the other electrode such that OH radicals are generated in the reaction vessel to which the water and the gas are supplied.

4. The pathogen and pest exterminating device of claim 1, wherein
the reaction vessel is formed in a tube shape, where the insertion part is inserted from an opening at one end, and the OH radicals are irradiated from an opening at the other end,
the insertion part is extended along a length direction of the reaction vessel, and
the other electrode is provided along a lateral surface of the reaction vessel, and a length of a portion that opposes the insertion part is from 80 mm to 1000 mm.

5. The pathogen and pest exterminating device of claim 1, wherein an evaporation rate of the water supplied from the water supply unit in the reaction vessel is 90 μl/min or higher.

6. A reaction vessel of a pathogen and pest exterminating device, comprising an opening part for supplying each of water and gas, which will become plasma, to the inside, and a pair of electrodes, wherein
one of the electrodes comprises an insertion part to be inserted into the reaction vessel from the opening part,
the other electrode is arranged at a position that opposes the insertion part, and
the insertion part is formed in a shape that restricts, between itself and the other electrode, a flow rate of the water supplied from the opening part.

7. The reaction vessel of a pathogen and pest exterminating device of claim 6, wherein the insertion part is formed in a coil, waveform, or mesh shape.

8. The pathogen and pest exterminating device of claim 2, wherein
the reaction vessel is formed in a tube shape, where the insertion part is inserted from an opening at one end, and the OH radicals are irradiated from an opening at the other end,
the insertion part is extended along a length direction of the reaction vessel, and
the other electrode is provided along a lateral surface of the reaction vessel, and a length of a portion that opposes the insertion part is from 80 mm to 1000 mm.

9. The pathogen and pest exterminating device of claim 3, wherein the reaction vessel is formed in a tube shape, where the insertion part is inserted from an opening at one end, and the OH radicals are irradiated from an opening at the other end, the insertion part is extended along a length direction of the reaction vessel, and the other electrode is provided along a lateral surface of the reaction vessel, and a length of a portion that opposes the insertion part is from 80 mm to 1000 mm.

10. The pathogen and pest exterminating device of claim 2, wherein an evaporation rate of the water supplied from the water supply unit in the reaction vessel is 90 μl/min or higher.

11. The pathogen and pest exterminating device of claim 3, wherein an evaporation rate of the water supplied from the water supply unit in the reaction vessel is 90 μl/min or higher.

12. The pathogen and pest exterminating device of claim 4, wherein an evaporation rate of the water supplied from the water supply unit in the reaction vessel is 90 μl/min or higher.

13. The pathogen and pest exterminating device of claim 8, wherein an evaporation rate of the water supplied from the water supply unit in the reaction vessel is 90 μl/min or higher.

14. The pathogen and pest exterminating device of claim 9, wherein an evaporation rate of the water supplied from the water supply unit in the reaction vessel is 90 μl/min or higher.

* * * * *